United States Patent
Chun

[19]

[11] Patent Number: 6,075,235
[45] Date of Patent: Jun. 13, 2000

[54] HIGH-RESOLUTION POLARIZATION-SENSITIVE IMAGING SENSORS

[76] Inventor: Cornell Seu Lun Chun, P.O. Box 2171, Inver Grove Heights, Minn. 55076-8171

[21] Appl. No.: 09/004,166

[22] Filed: Jan. 2, 1998

Related U.S. Application Data

[60] Provisional application No. 60/034,007, Jan. 2, 1997.

[51] Int. Cl.[7] .................................................. G02F 1/01
[52] U.S. Cl. ...................... 250/208.1; 250/225; 250/332; 250/341.3
[58] Field of Search .............................. 250/208.1, 225, 250/332, 334, 330, 336.1, 338.1, 339.01, 339.02, 339.14, 339.15, 340, 341.3, 347, 370.08; 356/369, 364; 244/3.17, 3.16, 3.15, 3.1

[56] References Cited

U.S. PATENT DOCUMENTS

| | | |
|---|---|---|
| 4,158,506 | 6/1979 | Collett . |
| 4,517,603 | 5/1985 | Epsztein . |
| 4,554,586 | 11/1985 | Tanuma . |
| 4,581,649 | 4/1986 | Morokawa . |
| 4,607,287 | 8/1986 | Endo . |
| 4,633,317 | 12/1986 | Uwira . |
| 4,638,371 | 1/1987 | Milch . |
| 4,652,928 | 3/1987 | Endo . |
| 4,755,876 | 7/1988 | Dangler . |
| 4,944,579 | 7/1990 | Egan . |
| 4,947,239 | 8/1990 | Kondou . |
| 4,967,264 | 10/1990 | Parulski . |
| 5,029,990 | 7/1991 | Egan . |
| 5,135,183 | 8/1992 | Whitney ................................. 244/3.16 |
| 5,180,912 | 1/1993 | McEwen . |
| 5,291,327 | 3/1994 | McEwen . |
| 5,301,042 | 4/1994 | Blanding . |
| 5,327,285 | 7/1994 | Faris . |
| 5,335,091 | 8/1994 | Palum . |
| 5,416,324 | 5/1995 | Chun . |
| 5,479,015 | 12/1995 | Rudman et al. ........................ 250/332 |
| 5,483,066 | 1/1996 | Sadjadi et al. ....................... 250/338.1 |
| 5,489,994 | 2/1996 | Torok . |
| 5,557,261 | 9/1996 | Barbour ................................. 340/580 |
| 5,557,324 | 9/1996 | Wolff . |
| 5,561,460 | 10/1996 | Katoh . |

OTHER PUBLICATIONS

Blommel, "The effects of microscan operation on staring infrared sensor imagery," in *Infrared Technology XVII*, Proc. SPIE 1540, 653–664 (1991).

(List continued on next page.)

*Primary Examiner*—John R Lee

[57] ABSTRACT

An apparatus and method to determine the surface orientation of objects in a field of view is provided by utilizing an array of polarizers and a means for microscanning an image of the objects over the polarizer array. In the preferred embodiment, a sequence of three image frames is captured using a focal plane array of photodetectors. Between frames the image is displaced by a distance equal to a polarizer array element. By combining the signals recorded in the three image frames, the intensity, percent of linear polarization, and angle of the polarization plane can be determined for radiation from each point on the object. The intensity can be used to determine the temperature at a corresponding point on the object. The percent of linear polarization and angle of the polarization plane can be used to determine the surface orientation at a corresponding point on the object. Surface orientation data from different points on the object can be combined to determine the object's shape and pose. Images of the Stokes parameters can be captured and viewed at video frequency. In an alternative embodiment, multi-spectral images can be captured for objects with point source resolution. Potential applications are in robotic vision, machine vision, computer vision, remote sensing, and infrared missile seekers. Other applications are detection and recognition of objects, automatic object recognition, and surveillance. This method of sensing is potentially useful in autonomous navigation and obstacle avoidance systems in automobiles and automated manufacturing and quality control systems.

19 Claims, 15 Drawing Sheets

OTHER PUBLICATIONS

Fortin, "Evaluation of the microscanning process," in *Infrared Technology XX*, Proc. SPIE 2269, 271–279 (1994).

McEwen, "A hand held imager for 2 dimensional detector arrays," in 4th International Conference on Advanced Infrared Detectors and Systems, IEE Conference Publication No. 321, pp. 105–111, Jun. 5–7, 1990, London.

Porter, "Ferroelectric arrays: the route to low cost uncooled infrared imaging," in *Infrared Technology XXI*, Proc. SPIE 2552, 573–582 (1995).

Walvern, "Polarization imagery," Optical Engineering, vol. 20, No. 1, 14–18 (1981).

Geary, "Parallel polarization processor," in *Polarization Considerations for Optical Systems*, Proc. SPIE 891, 74–78 (1988).

HIGH-RESOLUTION POLARIZATION-SENSITIVE IMAGING SENSORS

REFERENCE TO RELATED APPLICATION

This application claims the benefit of Provisional Patent Application Ser. No. 60/034,007 filed Jan. 2, 1997.

BACKGROUND OF THE INVENTION

1. Field of the Invention

The invention relates to imaging devices particularly with respect to the detection and recognition of remote objects.

2. Description of the Prior Art

Thermal imaging sensors are often used to search for and identify objects. These sensors capture the intensity of radiation from the surfaces of the objects. A fundamental limitation when using thermal intensity for search and identification is that thermal intensity gives one parameter whereas the surface orientation on a three-dimensional object is specified by two angles. Information about the two angles of surface orientation is often contained in the polarization of the thermal radiation. Polarization also gives useful information about the surface properties of the object. Man-made objects have unnaturally smooth surfaces, which in turn produces radiation with greater polarization. Natural backgrounds such as grass, trees, dirt, and sand generate radiation that is less polarized.

The polarization properties of a beam of incoherent radiation emitted or reflected from a object's surface can be completely described at a given wavelength by the four Stokes parameters, (I, Q, U, V). The first Stokes parameter I is a measure of the total intensity of radiation. The second parameter Q measures the amount of linear polarization in the horizontal direction. The third parameter U measures the amount of linear polarization at 45 degrees from the horizontal. She fourth parameter V is associated with the circular polarization.

The Stokes parameters I, Q, ani U can be transformed into percent of linear polarization P and angle of polarization plane $\phi$ using the relations, $$P = \frac{\sqrt{Q^2 + U^2}}{I} * 100 \quad (1)$$

$$\phi = \frac{1}{2} * \arctan\left(\frac{U}{Q}\right)$$

As described later, P and $\phi$ are directly related to the surface orientation of the object.

Conventional methods of determining polarization from images rely on the use of a single polarizer covering the entire imaging sensor. The polarizer is rotated and a sequence of image frames are captured. An example of this method is described in "Polarization imagery," by R. Walraven in Optical engineering, vol. 20 no. 1 (1981), pp. 14–18. Walraven uses a sequence of four image frames captured with a linear polarizer oriented at 0°, 45°, 90°, and 135°. The first three Stokes parameters can be determined at each image pixel, $$I = \frac{1}{2} \cdot (i_0 + i_{45} + i_{90} + i_{135})$$

$$Q = i_0 - i_{90}$$

$$U = i_{45} - i_{135}$$

where $i_x$ is the intensity measured with the polarizer oriented at x degrees.

A disadvantage to using a single polarizer is that the mechanism for rotation requires maintenance and is subject to failure during operation. Another disadvantage is that, because a large aperture polarizer is bulky, a high rotation speed is impractical, which limits how close in time the sequence of images can be captured. If the object is moving rapidly or the sensor system is vibrating, the object will be misregistered, i.e. in a different position in each image, in the sequence. A further disadvantage is that, the substrates on which polarizers are fabricated do not have plane parallel surfaces. When such substrates are rotated, the image position at the photodetectors will wander, resulting again in misregistration. Yet another disadvantage is that a sensor with a mechanism for rotating a polarizer at a high rotation speed would be massive and large and not portable.

A polarization-sensitive thermal imaging sensor which overcomes these disadvantages was disclosed by the present inventor in U.S. Pat. No. 5,416,324 (1995). This sensor is able to capture Stokes parameters I, Q, and U in a single image frame because the sensor uses an array of pixel-size polarizers in front of a two-dimensional focal plane array of photodetectors. Each pixel-size polarizer is a linear polarizer which is fixed in a rotated position relative to its nearest neighbors. Polarization data is derived from measuring the amounts of light which passes through polarizers with at least two different rotation orientations. The use of the polarizer array permits polarization data to be captured accurately, provided that the radiation from the object does not vary significantly from one pixel to its neighboring pixel. This would occur when objects extend over many pixels.

However, a disadvantage of using the polarizer array in the inventor's patent is that polarization data cannot be captured accurately when objects extend over less than one pixel, i.e. point source objects. This would be the case when attempting to detect an airplane at long range or when the detailed features on a object are important for its identification.

OBJECTS AND ADVANTAGES

Accordingly, besides the objects and advantages of the polarization-sensitive thermal imaging sensor described in the inventor's patent, several objects and advantages of the present invention are:

(a) to provide an imaging system which is able to capture polarimetric data for point source objects;

(b) to provide an imaging system which is able to capture polarimetric data for point source objects by their thermal emitted radiation;

(c) to provide an imaging system which is able to capture polarimetric data for point source objects in darkness;

(d) to provide an imaging system which is able to simultaneously capture three-dimensional information and temperature distribution with point source resolution;

(e) to provide an imaging system which is able to capture and display high-resolution polarimetric data in real time and with an update rate at video frequency; and (f) to provide a high-resolution polarimetric imaging sensor which is portable and can be mounted on a camera tripod.

Further objects and advantages of the present invention will become apparent from a consideration of the ensuing drawings and the descriptions.

SUMMARY OF THE INVENTION

An apparatus and method to determine the surface orientation of objects in a field of view is provided by utilizing an array of polarizers and two tilting plane parallel plates to microscan an image of the objects over the polarizer array. A sequence of image frames is captured. First, light radiated from a point on the surface of an object is incident on an element in the array, a linear polarizer oriented at 0°. The component of light which is transmitted by the polarizer is recorded in a first image frame. Then, by means of microscanning, the light is made incident on a second element in the array, a linear polarizer oriented at 45°. The component of light which is transmitted is recorded in a second image frame. Again, by means of microscanning, the light is made incident on a third element in the array, a linear polarizer oriented at 90°. The component of light which is transmitted is recorded in a third image frame. By combining the signal-s recorded in the three image frames, the intensity, percent of linear polarization, and angle of the polarization plane can be determined for radiation from each point on the object. The intensity can be used to determine the temperature at a corresponding point on the object. The percent of linear polarization and angle of the polarization plane can be used to determine the surface orientation at a corresponding point on the object. Surface orientation data from different points on the object can be combined to determine the object's shape and pose.

DETAILED DESCRIPTION

Figure 1:
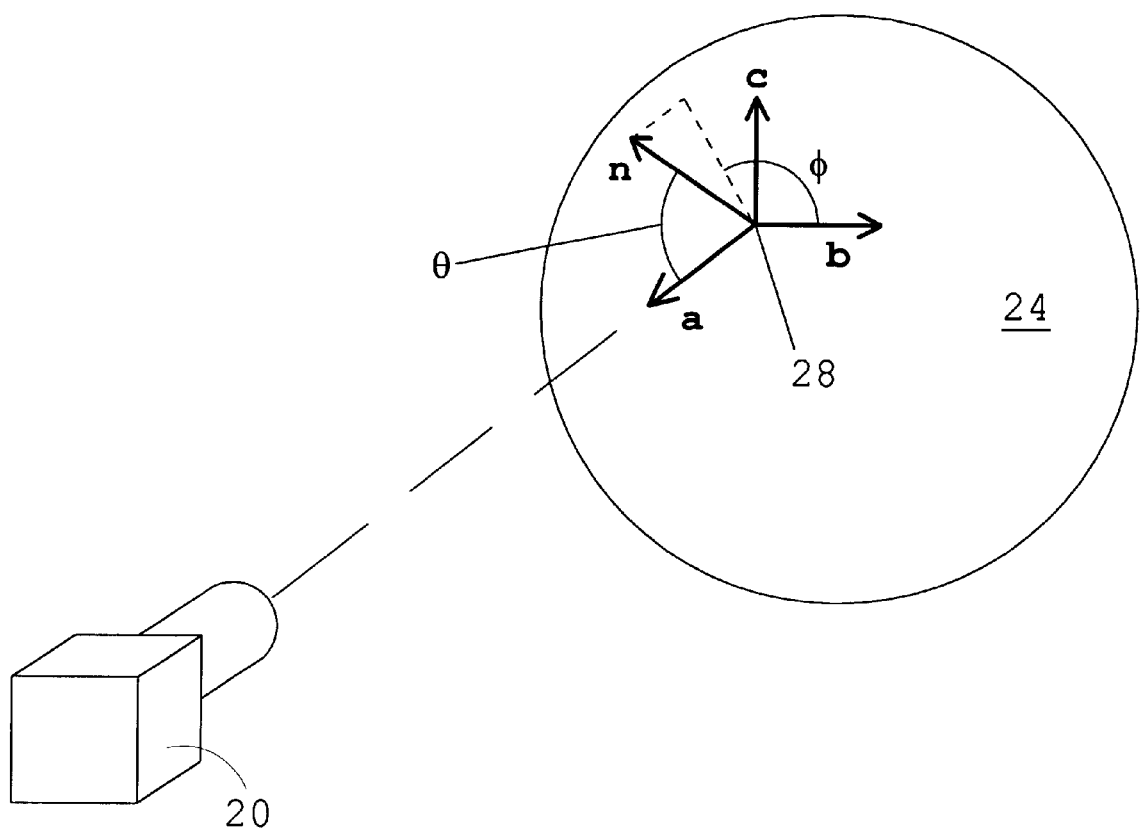
FIG. 1 is a perspective view of an object being imaged by a sensor.

FIG. 1 illustrates a typical situation encountered when using an imaging sensor for the detection and recognition of remote objects. A sensor 20 is viewing an object 24. Consider a point 28 herein called an object point on the surface of object 24 which is in the field of view of sensor 20. Define a vector a as the direction from the object point 28 to the sensor 20. Define vector b, perpendicular to a, as laying in the horizontal direction and pointing to the right relative to the view from the sensor 20. Define a vector c in the direction perpendicular to vectors a and b and pointing in the same direction as a right-handed vector cross product of a and b.

Next define n as a vector normal to the surface at object point 28. n is perpendicular to the plane tangent to the surface at object point 28. The surface orientation at object point 28 can be specified by determining two angles: θ defined as the angle between a and n, and φ defined as the angle between b and the projection of n onto the plane containing b and c. The paragraphs below will describe how θ and φ can be determined by measuring the amount of polarization in the thermal radiation emitted from object point 28 in the direction a.

Polarized thermal emission can be explained by relating to the more common experience of polarized reflection. When light is incident at a grazing angle on the surface of water the portion of the light which is reflected, as in sun glint, is linearly polarized with a horizontal plane of polarization. The portion of the light which is transmitted into the water is linearly polarized with a vertical plane of polarization. By the same mechanism, if light originates below the surface and passes through the surface, the transmitted light would be linearly polarized with a vertical polarization plane. The polarization plane contains the normal vector to the surface. The transmitted light when exiting at a more grazing angle to the surface will have a greater percent of polarization. Thermal emission is light originating below the surface.

Referring to FIG. 1, when thermal radiation is received by a polarization-sensitive sensor 20 from a surface element 28 on an object, the plane of polarization gives the angle φ and the percent of linear polarization P can be related to the angle θ. Together θ and φ determine the normal vector n to the surface element.

The relationship between P and θ can be found using the Fresnel equations for light transmission at a planar interface. Define the plane of emission as the plane containing the normal vector n to the surface element and the vector a from the surface point 28 to the sensor 20 [FIG. 1]. Using these equations, the emissivity $\epsilon_{//}$ for radiation linearly polarized parallel to the plane of emission and the emissivity $\epsilon_\perp$ for radiation linearly polarized perpendicular to the plane of emission are given by $$\epsilon_{//}(\theta) = \frac{4n_2 \cos\theta}{[(n_2^2 + \kappa_2^2)\cos^2\theta] + [2n_2\cos\theta] + 1}$$

$$\epsilon_\perp(\theta) = \frac{4n_2 \cos\theta}{\cos^2\theta + [2n_2\cos\theta] + n_2^2 + \kappa_2^2}$$

where θ is the angle between the surface normal n and the emission direction a [FIG. 1]. $n_2$ and $\kappa_2$ are the real and imaginary components of the complex index of refraction defined as $n_2 - i\kappa_2$. The percent of polarization is $$P(\theta) = \frac{\varepsilon_{//}(\theta) - \varepsilon_{\perp}(\theta)}{\varepsilon_{//}(\theta) + \varepsilon_{\perp}(\theta)} \cdot 100$$

Figure 2:
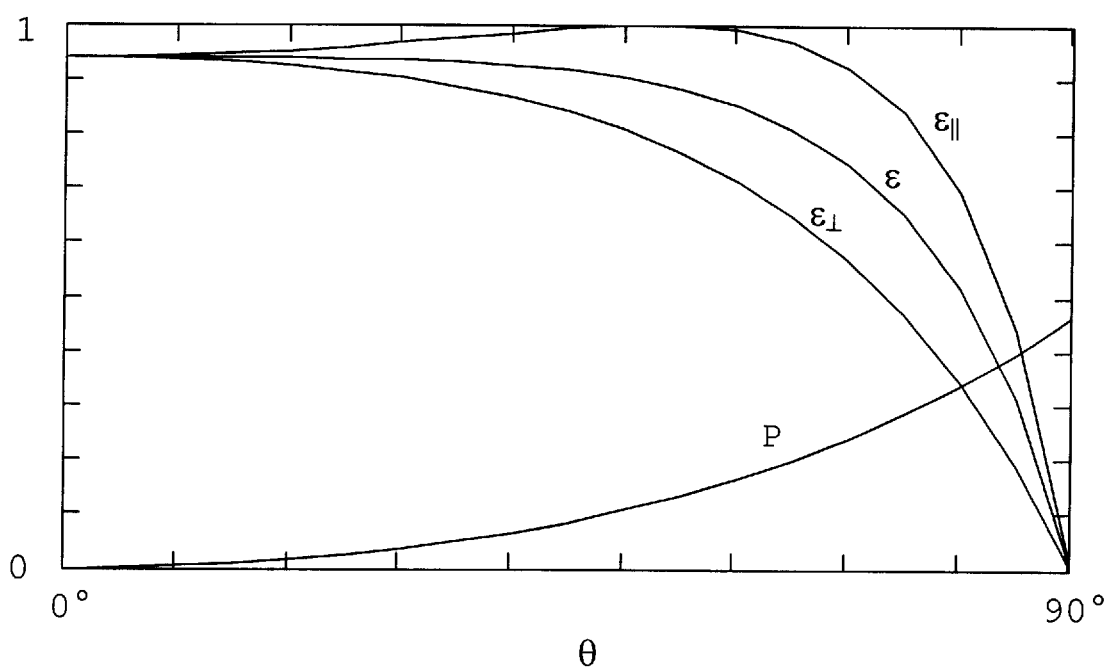
FIG. 2 is a graph representing the relationship between percent of polarization and angle of emission for a dielectric surface.

Using the complex index of refraction for a typical dielectric paint, $\varepsilon_{//}$, $\varepsilon_{\perp}$, and P can be calculated and are shown in FIG. 2. As is apparent from FIG. 2, a measurement of P will determine the angle θ.

What follows is a description of a method and apparatus for determining θ and φ simultaneously at a plurality of object points, thereby enabling the recognition of objects by their shapes and poses.

Figure 3:
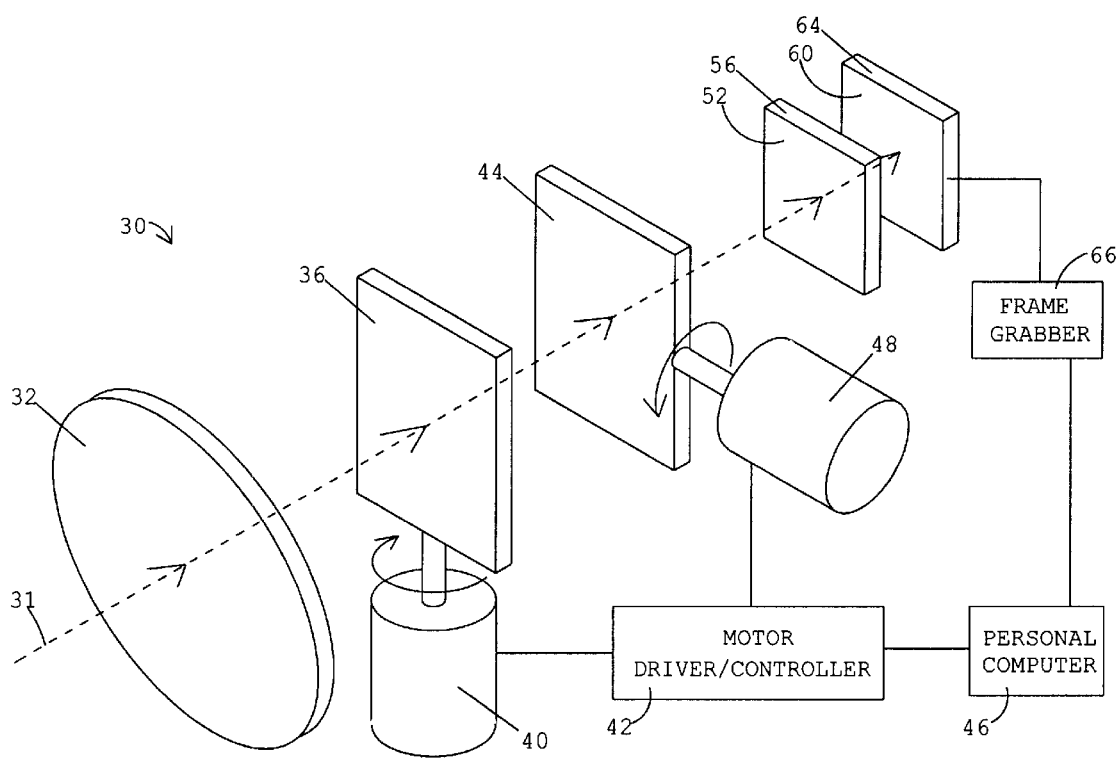
FIG. 3 is a perspective view of a polarization-sensitive imaging sensor using tilting plane parallel plates for microscanning.

FIG. 3 shows a polarization-sensitive imaging sensor 30 using the method of the present invention. Light 31 from objects in the field of view is transmitted through a focusing lens 32. The radiation then passes through a transparent plane parallel plate 36 which can be rotated about a vertical axis by stepping motor 40. The radiation passes through a second transparent plane parallel plate 44 which can be rotated about a horizontal axis by stepping motor 48. The radiation then passes through an array of polarizers 52 which is supported on a transparent substrate 56. The light then forms an image on a two-dimensional array of photodetectors 60, called a focal plane array, supported on a substrate 64.

Figure 4:
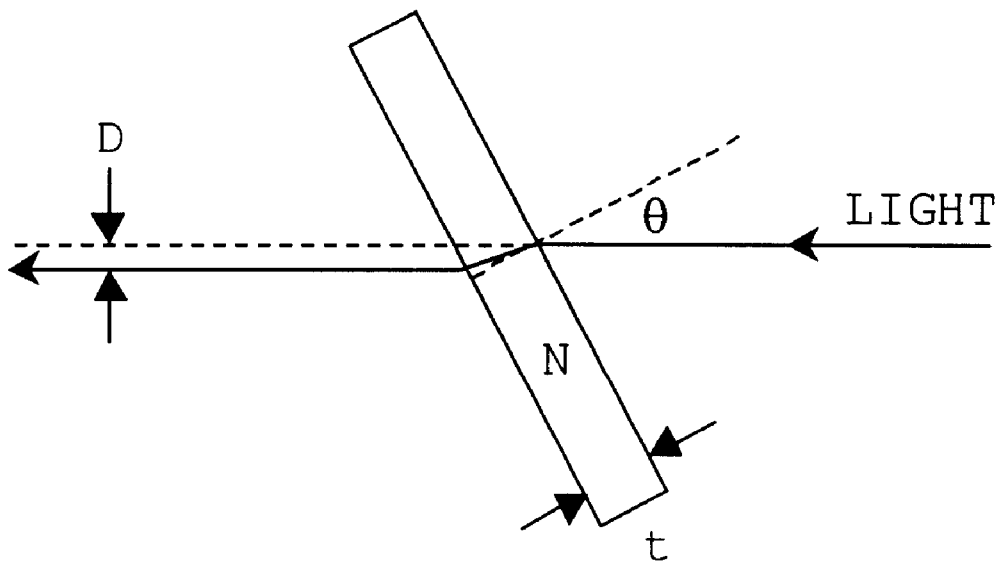
FIG. 4 is a cross sectional side view of a tilted plane parallel plate showing how transmitted light is displaced.

The plane parallel plates 36 and 44 serve to displace laterally the image on the focal plane array 60. Rotation of plate 36 about a vertical axis will cause the image to be moved in the horizontal direction. As shown in FIG. 4, when light rays pass through a plane parallel plate of index of refraction N, of thickness t, and tilted at an angle θ, the rays are displaced by distance D. Displacing the image over small distances is call microscanning. Similarly rotation of plate 44 about a horizontal axis will cause the image to be moved in the vertical direction.

Stepping motors 40 and 48 are controlled and powered by a motor driver and controller 42. The driver/controller is connected to a central processing unit, such as a personal computer 46. The images captured by the focal plane array 60 is transferred to a frame grabber 66. The image data is further transferred from the frame grabber 66 to the computer 46. The personal computer 46 controls the operation of the stepping motors 40 and 48 and the frame grabber 66.

Focal plane array sensors are available commercially in large formats for high resolution imaging. For visible wavelengths there are charge coupled device (CCD) cameras. In the midwave infrared range there are PtSi and InSb sensors. And in the longwave infrared range there are HgCdTe and microbolometer cameras.

Figure 5:
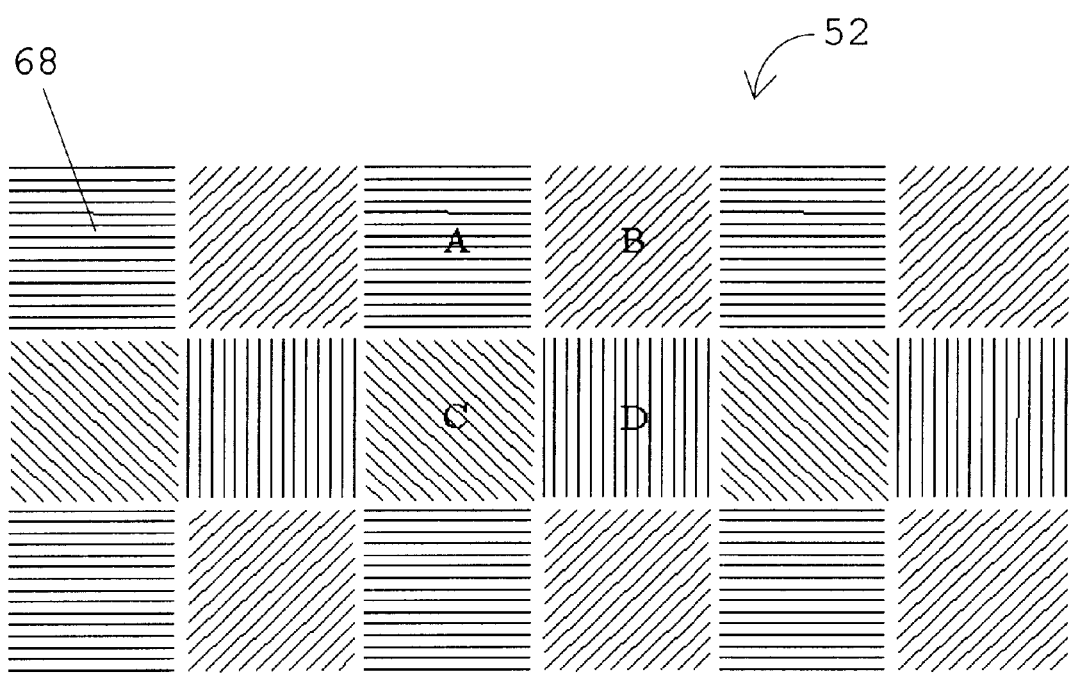
FIG. 5 is a plan view of a portion of a two-dimensional polarizer array formed from wire grids.
Figure 6:
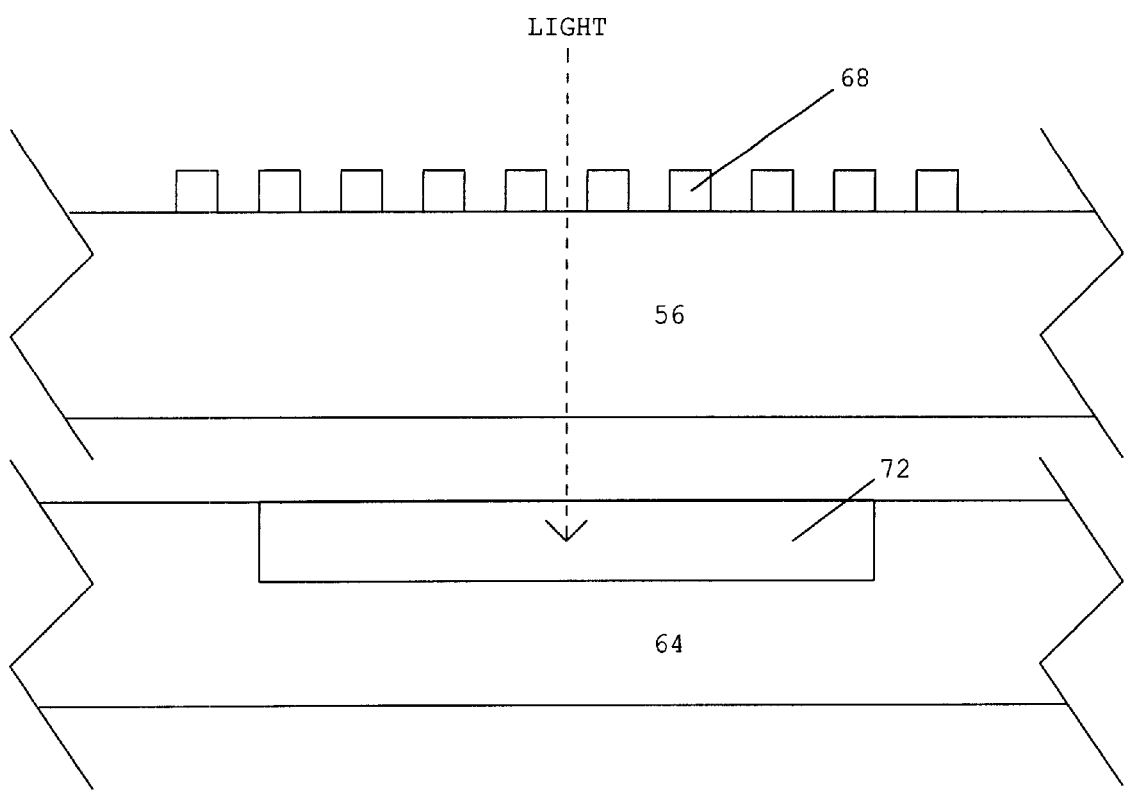
FIG. 6 shows a cross sectional side view of an embodiment where polarizer and photodetector are supported by separate substrates.

The array of polarizers 52 is shown in greater detail in FIG. 5. Each polarizer element 68 corresponds to a detector element in the two-dimensional array of photodetectors 60. As shown in FIG. 6, the two arrays are placed in close proximity such that all radiation which is incident on photodetector 72 much first be transmitted through the corresponding polarizer element 68.

Each element of the polarizer array 52 is fixed in orientation such that each element transmits a different polarization plane than the element's nearest neighbor elements and next nearest neighbor elements. In particular, in FIG. 5 polarizer D transmits a horizontal or 0° plane of polarization. It's nearest neighbor C transmits a 45° plane of polarization. Another nearest neighbor B transmits 135°. The next nearest neighbor A transmits a vertical or 90° plane of polarization.

Figure 7:
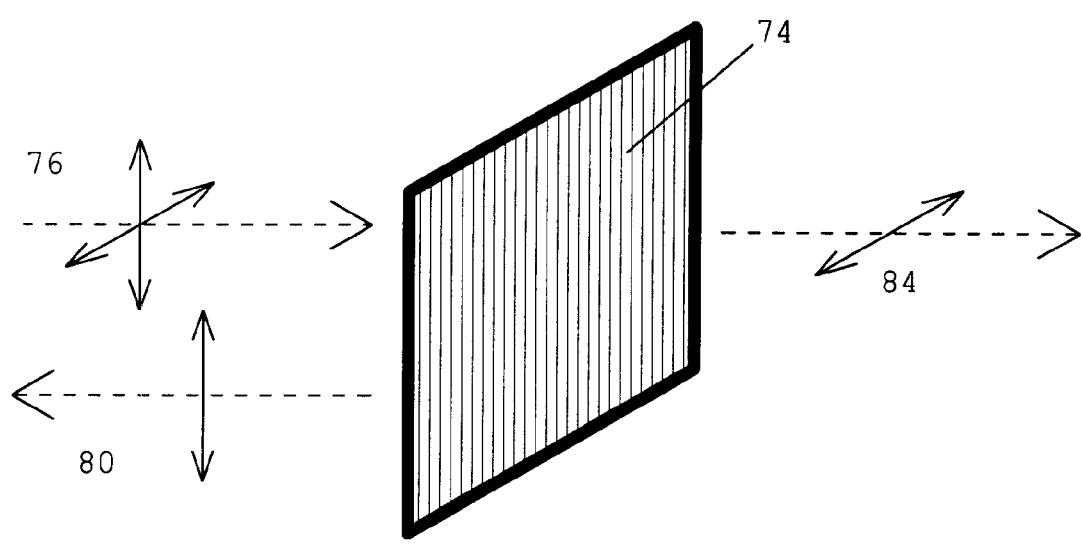
FIG. 7 shows the operation of a wire grid polarizer.

A practical realization of the polarizer array 52 is as an array of wire grids. Wire grid polarizers are know in the art and their operation can be described with reference to FIG. 7. A wire grid polarizer 74 is a set of parallel metal wires with spacings between adjacent wires much less than the wavelength of the incident light 76. The component of incident light 76 with plane of polarization parallel to the wires is reflected, indicated in FIG. 7 as reflected light 80. The component of incident light 76 with plane of polarization perpendicular to the wires is transmitted as indicated by transmitted light 84.

In practice, an array 52 of wire grid polarizers can be formed on a single, planar, transparent substrate 56 using the techniques of depositing metal films and microlithographic patterning. These techniques are well established for the fabrication of integrated circuits.

OPERATION OF THE PREFERRED EMBODIMENT

Figure 8:
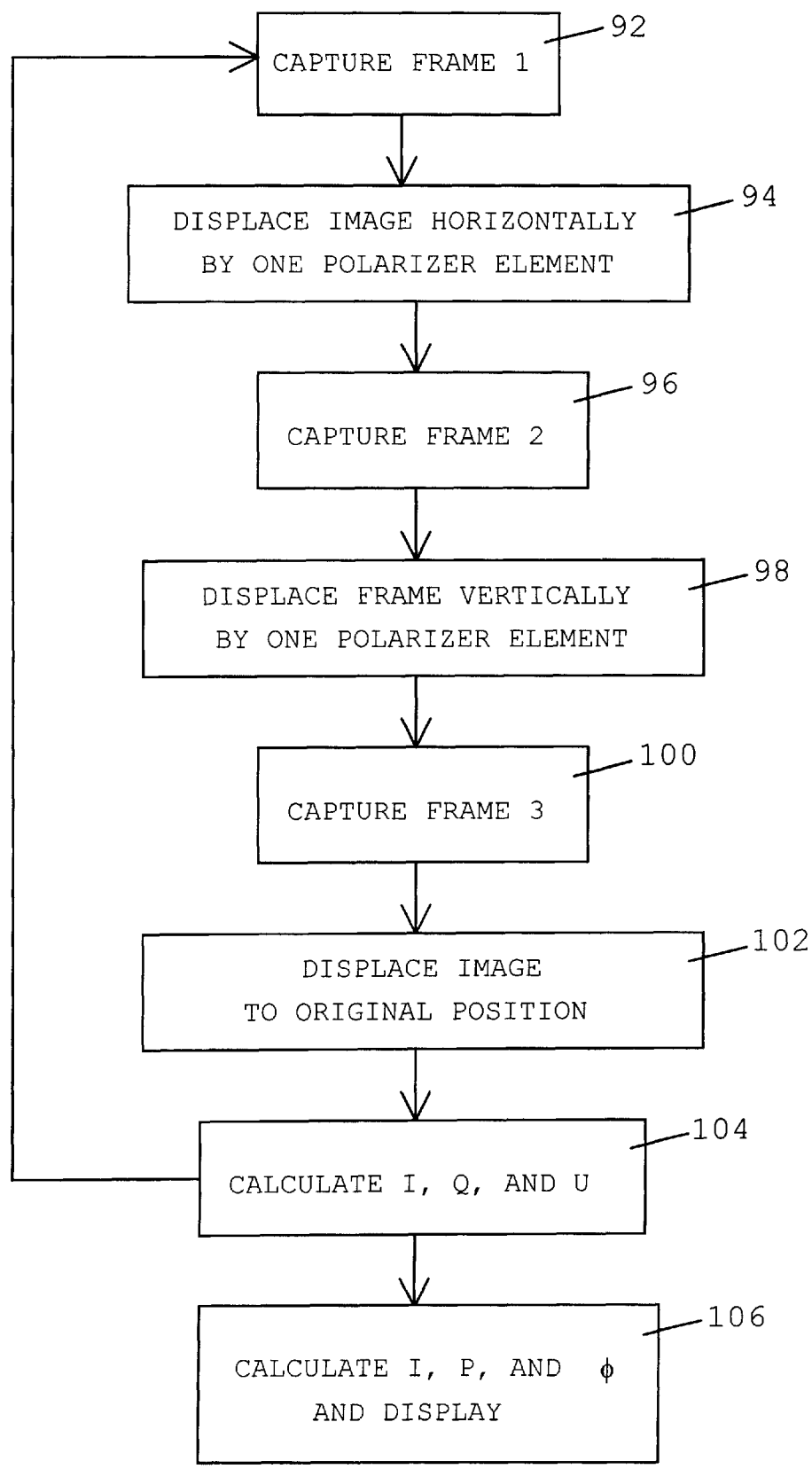
FIG. 8 is a flowchart showing the operations for acquiring polarization data.

The imaging sensor 30 in FIG. 3 is used to capture data on the Stokes parameters I, Q, and U over the field of view. The sequence of operations for capturing polarization data is shown in FIG. 8. These operations can be entered as a sequence of instructions in a program for the personal computer 46 to execute.

Figure 9:
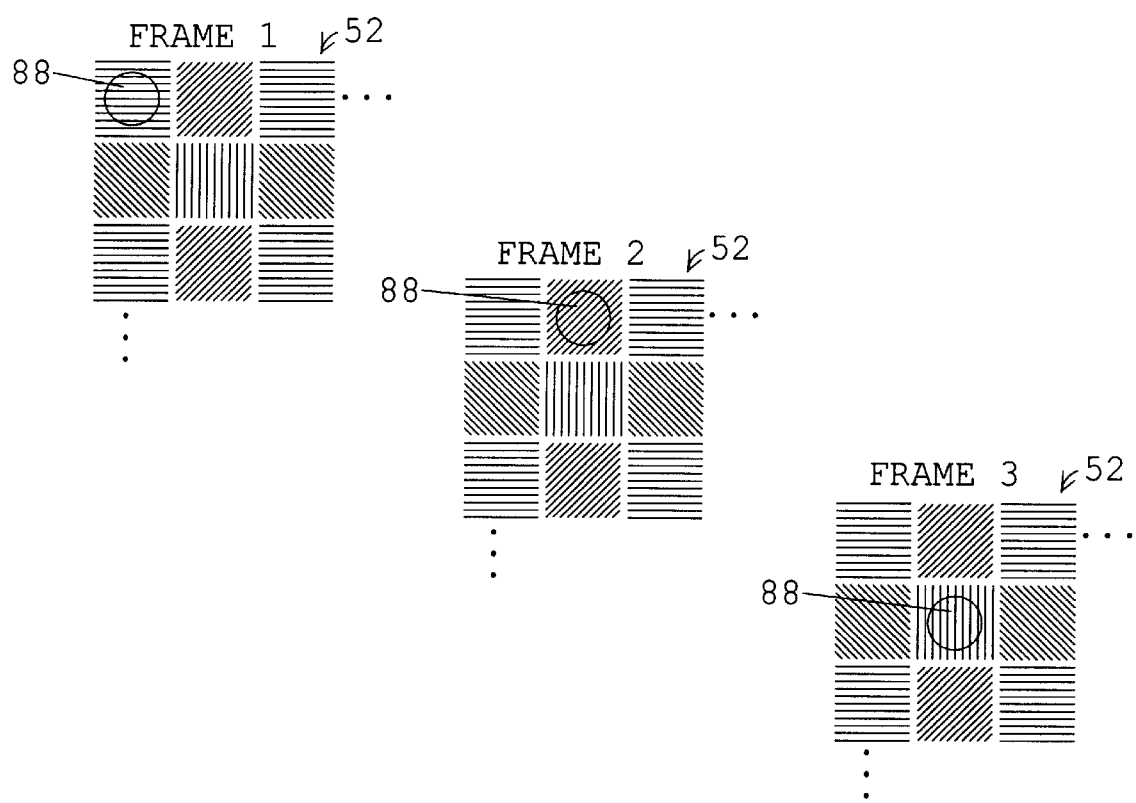
FIG. 9 shows plan views of the two-dimensional polarizer array and the location of the image of a point source object for a sequence of three image frames.

Before this program begins execution, the imaging sensor 30 in FIG. 3 has the following configuration. The focusing lens 32 forms an image of the objects on the focal plane array 60. An individual photodetector in the focal plane array 60 views a object point through the detector's corresponding polarizer. In FIG. 9, the view of polarizer array labeled Frame 1 shows the location of the image 88 of the object point. The image 88 is on a 90° polarizer. Call this the original position of the object point's image.

When the computer program is executed, the first instruction 92 in FIG. 8 is to the frame grabber 66 to capture an image frame, labeled Frame 1. The image frame is an array of numbers, each number is related to the intensity of the radiation incident on a photodetector in the focal plane array 60. Frame 1 is stored in electronic memory in the computer 46.

The next instruction 94 is to the stepping motor driver/controller 42. The driver/controller 42 will cause the stepping motor 40 to rotate the plane parallel plate 36 by an angle such that the image 88 of the object point in FIG. 9 is moved horizontally to a neighboring polarizer in the array 52. The image 88 is now on a 135° polarizer as shown in the view labeled Frame 2 in FIG. 9.

Instruction 96 is to the frame grabber 66 to capture and store Frame 2. Instruction 98 is to the driver/controller 42 to cause motor 48 to rotate the plate 44. Image 88 is this time moved vertically to a neighboring polarizer in the array 52. FIG. 9 shows the image 88 now on a 0° polarizer. Frame 3 is captured and stored during instruction 100.

In instruction 102, the driver/controller 42 cause motors 40 and 48 to rotate to their original positions. The image 88 of the object point is returned to its original position on the 90 polarizer. Instruction 104 is for the computer to calculate the Stokes parameters I, Q, and U over the field of view. For radiation from the object point contributing to image 88 in FIG. 9, I, Q, and U are calculated from Frames 1, 2, and 3 using the equations, $I = i_0 + i_{90}$ $Q = i_0 + i_{90}$ $U = (-2 \cdot i135) + i_0 + i_{90}$ where $i_x$ is the intensity measured after the radiation from the object point is transmitted through a polarizer oriented at x degrees.

The I, Q, and U data is then stored and the computer returns to instruction 92. The I, Q, and U data can be transformed using Equations (1) into intensity I, percent of linear polarization P, and angle φ of the polarization plane as in instruction 106. The polarization data can be displayed on monitor of the computer 46.

The instructions 92 to 106 can be executed very quickly with presently available computer hardware and stepping motors. The display in instruction 106 can be updated at nearly video frequencies. Commercially available stepping motors are lightweight and compact. The imaging system 30 in FIG. 3 will be portable, and the optical components can be placed on a tripod.

ALTERNATIVE EMBODIMENTS

There are alternative means for performing the microscanning in the imaging sensor 30 of FIG. 3. The plane parallel plates 36 and 44 can be replaced by a single plane parallel plate. The single plate can be rotated along the horizontal and vertical axes using linear translation devices. These translation devices can be piezoelectric, voice coil, or magnetic solenoid actuators.

Actuators can be eliminated by replacing the single plane parallel plate with a sequence of tilted plane parallel plates placed on the rim of a wheel. The wheel is spinning at a constant rate with the wheel's axis parallel to the optic axis of the imaging sensor. Only one tilted plate is in the optical path at any moment. As the wheel spins successive plates enter the optical path, causing the image on the polarizer array 52 to be displaced. Such an arrangement of plates on a wheel is described in U.S. Pat. No. 5,180,912 to McEwen et al.

In U.S. Pat. No. 5,561,460 to Katoh et al. a single transparent plane parallel plate is held at a constant angle relative to optic axis. To perform the microscanning, the plate is rotated about the optic axis. This microscanning technique can be used in the present invention.

Figure 10:
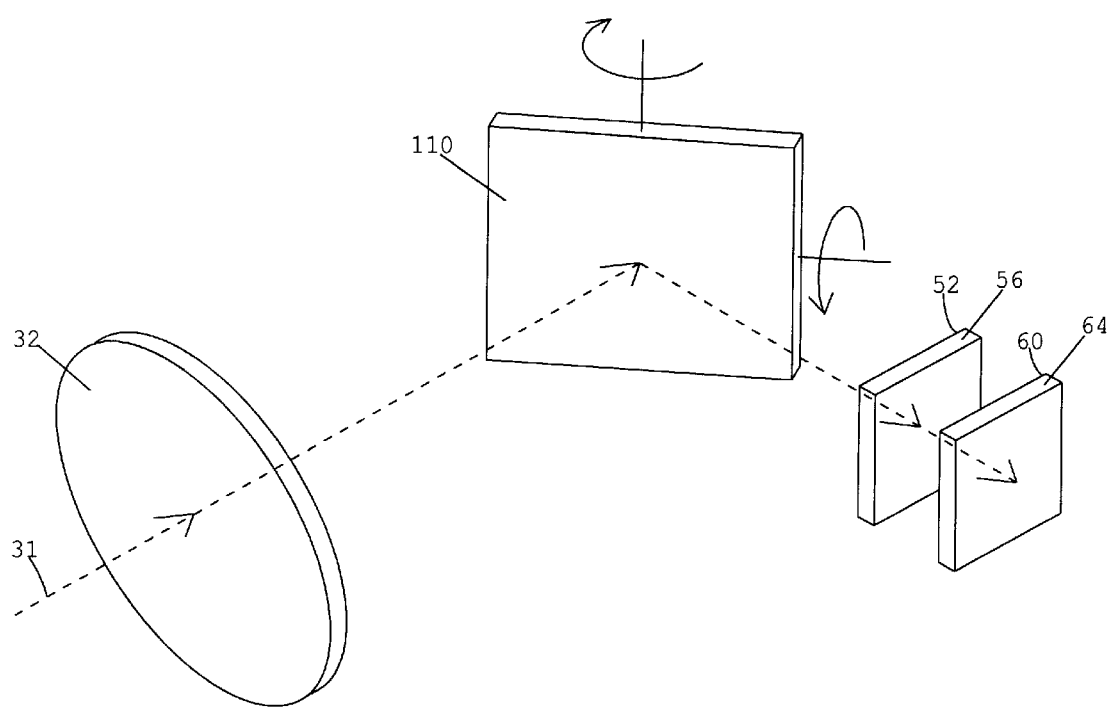
FIG. 10 is a perspective view of a polarization-sensitive imaging sensor using a tilting mirror for microscanning.

Another embodiment has optical path of the imaging sensor 30 of FIG. 3 folded. This is shown in FIG. 10. The plane parallel plates 36 and 44 are replace by a planar mirror 110. To cause the microscanning, the mirror is rotated along the horizontal and vertical axes. The rotation of the mirror can be performed by linear translation devices such as piezoelectric, voice coil, or magnetic solenoid actuators. Microscanning using a mirror is described in F. P. Blommel et al., "The effects of microscan operation on staring infrared sensor imagery," in *Infrared Technology XVII*, Proc. SPIE 1540, 653–664 (1991).

Figure 11:
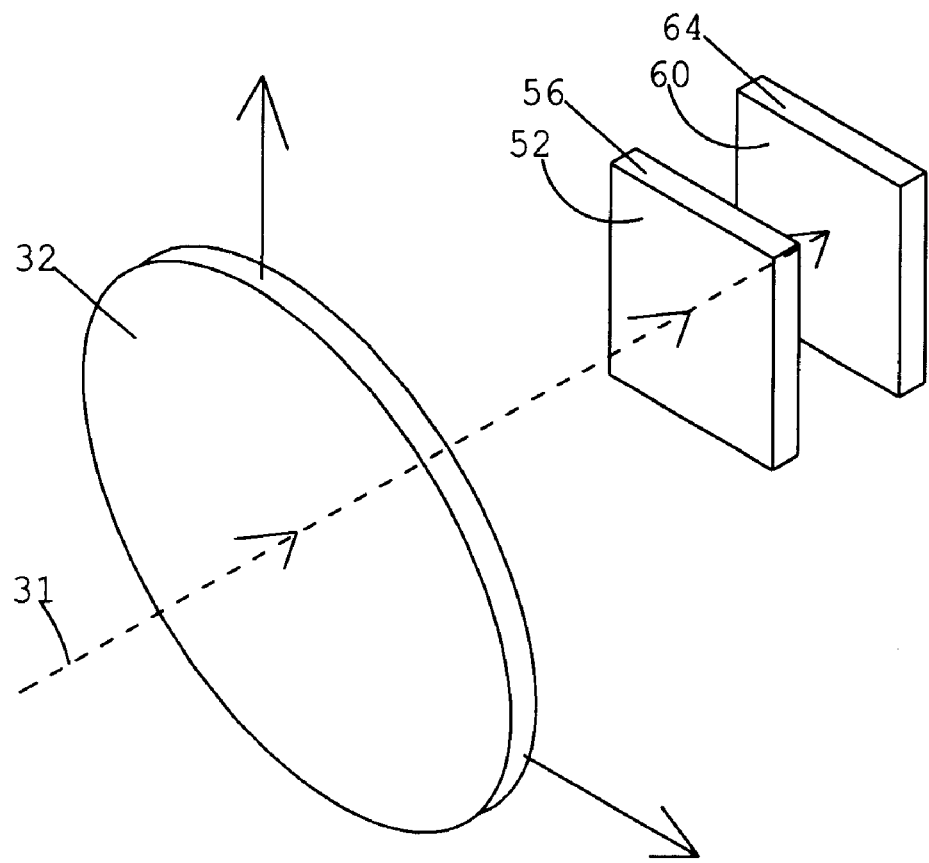
FIG. 11 is a perspective view of a polarization-sensitive imaging sensor using lateral translation of the imaging lens for microscanning.

In yet another embodiment shown in FIG. 11, the image on the two-dimensional polarizer array 52 is displaced by translating the focusing lens 32 in the horizontal and vertical direction. The movement of the focusing lens 32 can be performed using linear translation devices such as piezoelectric, voice coil, or magnetic solenoid actuators. Microscanning using a lens is described in J. Fortin et al., "Evaluation of the microscanning process," in *Infrared Technology XX*, Proc. SPIE 2269, 271–279 (1994).

In the art, microscanning almost exclusively refers to the displacement of an image on a focal plane array by a distance equal to a fraction of the pitch between photodetectors. However, microscanning in the present invention is the displacement of an image on a polarizer array by a distance equal to the pitch between polarizers.

SCOPE OF INVENTION

Although the embodiments described referred to the processing and sensing of light, the present invention is applicable to the processing and sensing of other forms of electromagnetic radiation, such as microwave, millimeter wave, and x-rays.

In the embodiments described above, the imaging sensor 30 in FIG. 3 contains a two-dimensional array of linear polarizers 52. The linear polarizer is an example of a filter. A filter is a device which transmits selected components of the electromagnetic radiation which is incident.

Figure 12:
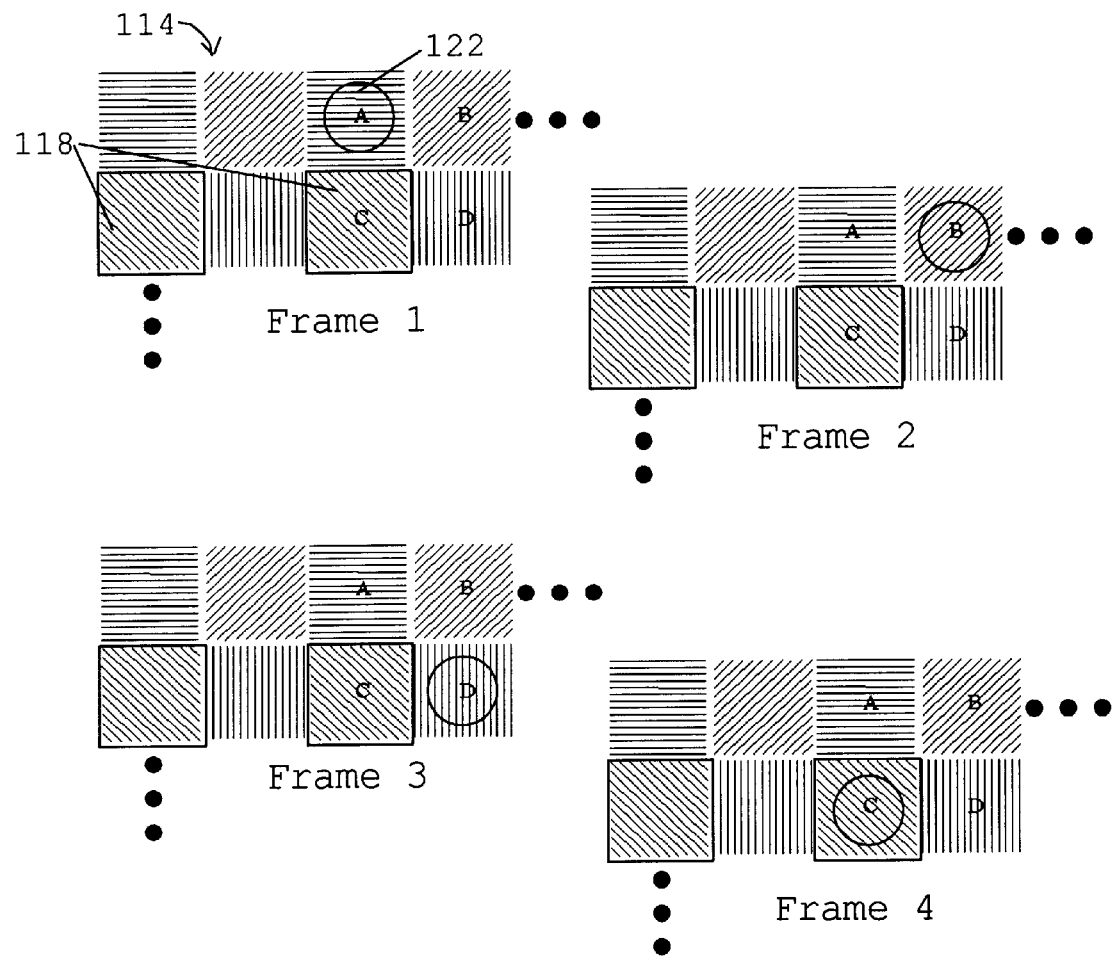
FIG. 12 shows a plan view of an array of linear polarizers and waveplates/polarizer combinations and the location of the image of a point source object for a sequence of four image frames.

A type of polarization filter is a combination of a quarterwave retarder followed by a linear polarizer. FIG. 12 shows a view of a filter array 114 where such a retarder/polarizer combination 118 is included with linear polarizers. Light from an object point is focused by the imaging lens 32 to an image 122 on the filter array 114. Four frames are captured with microscan displacements between each frame. The image 122 of the object point is incident on filter array elements A, B, C, and D in Frames 1, 2, 4, and 3 respectively. The photodetector signals at A, B, C, and D give the intensities $i(90°,0°)$, $i(135°,0°)$, $i(45°,90°)$, and $i(0°,0°)$ respectively where the first argument is the angle of rotation of the wire grid polarizer and the second is the phase change in the electromagnetic waves due to the retarder. For light radiated from the object point, the Stokes parameters are $$I=i(0,0)+i(90,0)$$

$$Q=i(0,0)+i(90,0)$$

$$U=I-(2\cdot i(135,0))$$

$$V=I-(2\cdot i(45,90))$$

Hence, with this technique the four Stokes parameters can be captured over the field of view with point source resolution.

As mentioned above, a filter is a device which transmits selected components of the electromagnetic radiation which is incident. These components can be components of wavelength as well as components of polarization. For example, there can be four types of wavelength filters, W1, W2, W3, and W4, arranged in an array. Each type of filter transmits a selected range of wavelengths. The output from such a imaging sensor would be a spectral characterization of the radiation from objects in the field of view.

Figure 13:
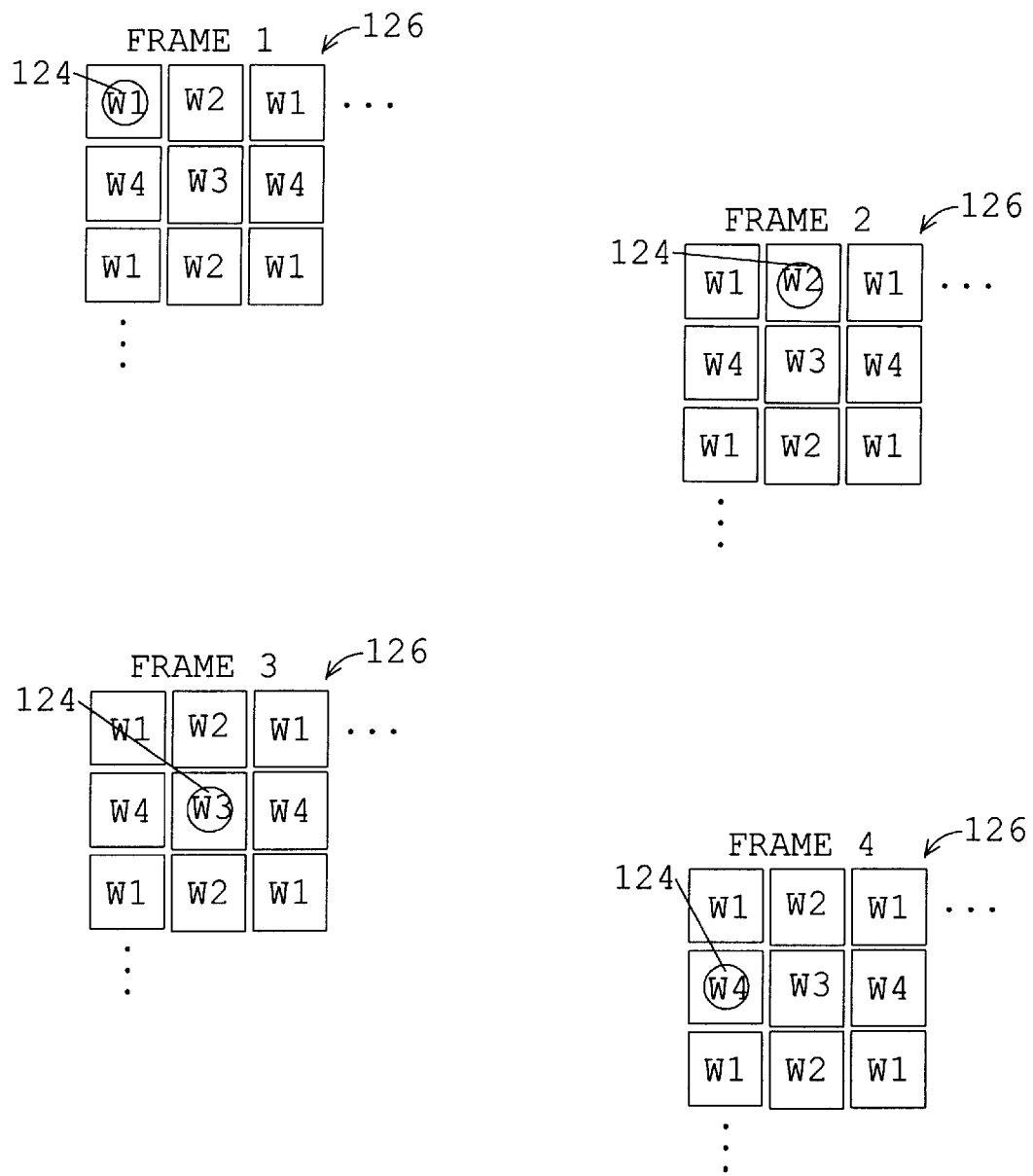
FIG. 13 shows a plan view of an array of four types of wavelength filters and the location of the image of a point source object for a sequence of four image frames.

The operation of such a multi-spectral imaging sensor is shown in FIG. 13. The image 124 of an object point is incident on filter W1 in array 126 when Frame 1 is captured. Then the image is displaced by microscanning, so that the image of the object point is incident on filter W2 in Frame 2, on filter W3 in Frame 3, and on filter W4 in Frame 4. A computer can combine Frames 1, 2, 3, and 4 into a map over the field of view of the spectral characteristics of the objects.

Figure 14:
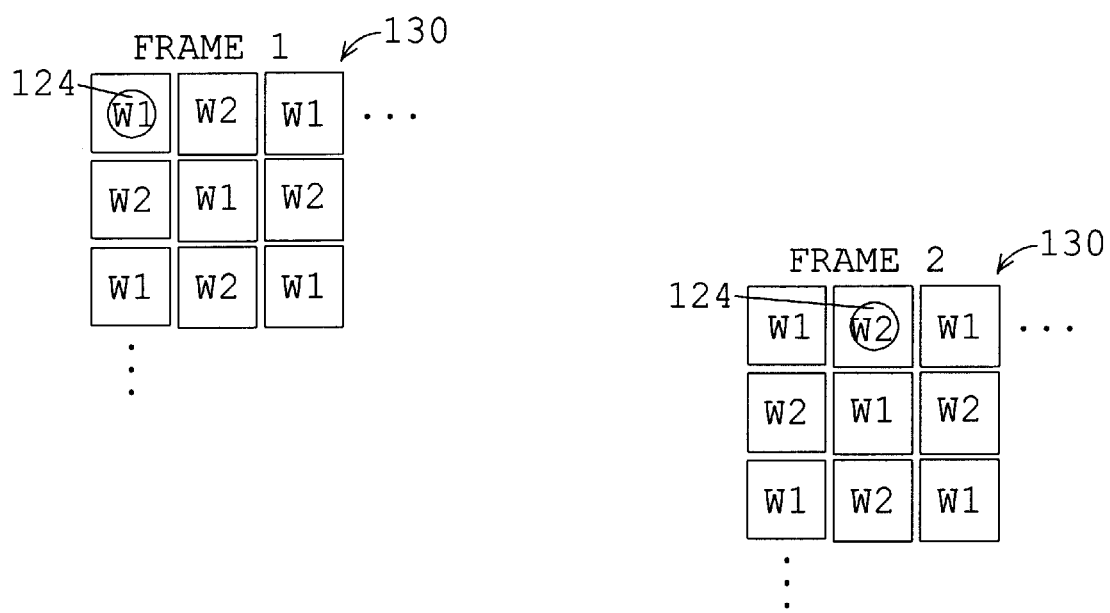
FIG. 14 shows a plan view of an array of two types of wavelength filters and the location of the image of a point source object for a sequence of two image frames.

If only two wavelength ranges are of interest, then an array with two types of filters, W1 and W2, can be used. Such a filter array 130 is shown in FIG. 14. The arrangement of filters in array 130 is similar to a checkerboard with W1 filters located at red squares and W2 at black squares. The image 124 of an object point is incident on filter W1 when Frame 1 is captured. Then the image is displaced by microscanning, so that the image of the object point is incident on filter W2 in Frame 2. A computer can combine Frames 1 and 2 to produce data on the wavelenghts radiated by objects in the field of view.

Figure 15:
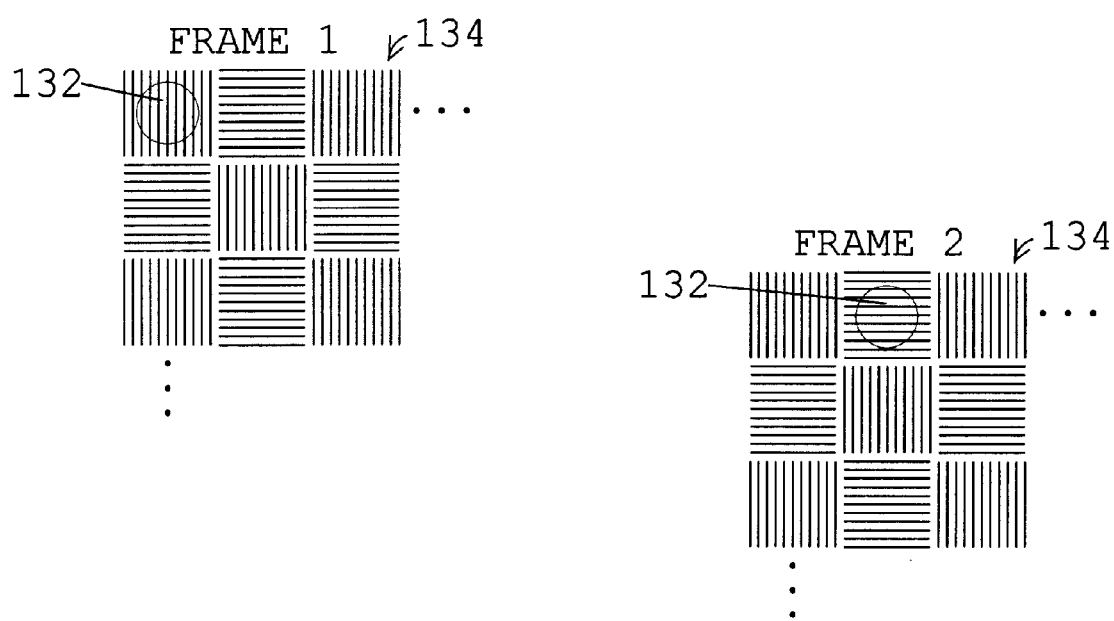
FIG. 15 shows a plan view of an array of horizontal and vertical polarizers and the location of the image of a point source object for a sequence of two image frames.

Returning to filters which transmit selected polarization components, if only the Stokes parameters I and Q are of interest, then the wire grid polarizer array 134 in FIG. 15 can be used. The image 132 of an object point is incident on a 0° polarizer when Frame 1 is captured. Then the image is displaced by microscanning, so that the image of the object point is incident on a 90° polarizer in Frame 2. A computer can combine Frames 1 and 2 to calculate $$I = i_0 + i_{90}$$
$$Q = i_0 - i_{90}$$

over the field of view.

While the invention has been described in its preferred embodiments, it is understood that the words which have been used are words of limitations and that changes within the purview of the appended claims may be made without departing from the scope and spirit of the invention in its broader aspects.

What is claimed is:

1. Apparatus for obtaining data concerning the characteristics of objects within a field of view comprising:
   (a) an array of filters for receiving and filtering electromagnetic waves,
   (b) means for directing electromagnetic waves from object points so as to be incident electromagnetic waves on said array of filters configured such that each filter of said array is exposed to incident electromagnetic waves originating only from a respective object point,
   (c) means for detecting said incident electromagnetic waves as filtered electromagnetic waves transmitted through said filters and producing signals indicative of a parameter thereof,
   (d) means for microscanning, including means for displacing said incident electromagnetic waves relative to said array of filters such that said incident electromagnetic waves originating from a particular object point, and having been incident on a first filter of said filter array, are made incident on at least a second filter of said filter array which is a neighbor of said first filter, and
   (e) means for combining a plurality of signals from said detecting means to produce an image of an object in the field of view.

2. The apparatus of claim 1, wherein said means for combining a plurality of signals from said detecting means includes means to combine signals produced by incident electromagnetic waves originating from an object point and passing through at least two elements in said array of filters.

3. The apparatus of claim 1, wherein said array of filters comprises a two-dimensional array of linear polarizers.

4. The apparatus of claim 1, wherein said means for detecting said incident electromagnetic waves comprises a two-dimensional array of photodetectors.

5. The apparatus of claim 1, wherein said means for displacing said incident electromagnetic waves relative to said plurality of filters comprises at least one transparent plane parallel plate and at least one mechanized control device for the rotation of said at least one transparent plane parallel plate.

6. The apparatus of claim 3, wherein said two-dimensional array of linear polarizers includes polarizers oriented at 0°, 45°, 90°, and 135°, each polarizer having a different orientation from proximate neighboring polarizers.

7. The apparatus of claim 2, wherein said means for combining a plurality of signals from said detecting means yields output signals corresponding to data including at least one of intensity, percent of polarization, and angle of polarization plane of said waves originating from said object point.

8. The apparatus of claim 5, wherein said means for combining a plurality of signals from said detecting means yields output signals corresponding to the orientation of the plane tangent to the surface of said object in the field of view at said object point.

9. The apparatus of claim 8, further including means for combining a plurality of signals corresponding to the orientations of the tangent planes at two or more object points to yield output signals corresponding to the shape of objects in the field of view contributing said object points.

10. A method for obtaining data concerning the characteristics of objects within a field of view comprising the steps of:
    (a) directing electromagnetic waves from object points onto an array of filters wherein each filter in said array is exposed only to electromagnetic waves originating from a respective object point,
    (b) detecting said waves transmitted through said filters,
    (c) displacing said directed electromagnetic waves relative to said array of filters such that said waves originating from an object point and having been incident on a first filter in said filter array is made incident on a second filter in said filter array which is a neighbor of said first filter,
    (d) combining a plurality of signals from said detecting means, said plurality of signals having been caused by said waves originating from an object point and passing through one or more filters in said array of filters.

11. The method of claim 10, wherein said array of filters is a two-dimensional array of linear polarizers.

12. The method of claim 10, wherein said waves transmitted through said filters are detected by a two-dimensional array of photodetectors.

13. The method of claim 11, wherein said directed electromagnetic waves are displaced relative to said plurality of filters by the rotation of at least one transparent plane parallel plate.

14. The method of claim 13, wherein said two-dimensional array of linear polarizers includes polarizers oriented at 0°, 45°, 90°, and 135°, each said polarizer having a different orientation than neighboring said polarizers.

15. The method of claim 14, wherein said plurality of signals having been caused by said waves originating from an object point are combined to yield output signals corresponding to data including at least one of intensity, percent of polarization, and angle of polarization of said waves originating from said object point.

16. The method of claim 14, wherein said plurality of signals having been caused by said waves originating from an object point are combined to yield output signals corresponding to the orientation of the plane tangent to the surface at said object point.

17. The apparatus of claim 16, further including combining a plurality of signals corresponding to the orientations of the tangent planes at two or more object points to yield output signals corresponding to the shape of objects contributing to said object points.

18. Apparatus for obtaining data concerning the characteristics of objects within a field of view comprising:
    (a) a two-dimensional filter array of linear polarizers,
    (b) a lens system for receiving electromagnetic waves from objects in a field of view and forming an image of said objects on said two-dimensional array of linear polarizers, said filter array including polarizers oriented at 0°, 45°, 90°, and 135°, each polarizer having a different orientation from neighboring polarizers,
    (c) a two-dimensional detector array of photodetectors for detecting said electromagnetic waves as transmitted through said polarizers, (d) at least one rotating transparent plane parallel plate for displacing said image of said objects relative to said filter array such that said electromagnetic waves originating from an object point and having been incident on a first one of said polarizers is made incident on a second one of said polarizers which is a neighbor of the said first one of said polarizers, (e) a computer for combining a plurality of signals from said detector array to yield data corresponding to the orientation of the plane tangent to the surface at an object point, said plurality of signals having been produced by said electromagnetic waves originating from said object point and passing through at least two elements in said polarizer array.

19. The apparatus of claim 18, wherein said computer combines a plurality of signals corresponding to the orientations of the tangent planes at two or more object points to yield output signals corresponding to the shape of objects in the field of view contributing to said object points.

* * * * *